US010781394B2

(12) United States Patent
Moniz et al.

(10) Patent No.: US 10,781,394 B2
(45) Date of Patent: Sep. 22, 2020

(54) LUBRICATING OIL COMPOSITIONS COMPRISING A BIODIESEL FUEL AND A MANNICH CONDENSATION PRODUCT

(71) Applicants: Chevron Oronite Technology B.V, San Ramon, CA (US); Chevron Oronite Company LLC, San Ramon, CA (US)

(72) Inventors: Menno Anton Stefan Moniz, Rotterdam (NL); Walter Alexander Hartgers, Rotterdam (NL); Richard Hogendoorn, Rotterdam (NL); Moussa Echankouki, Rotterdam (NL); Peter Kleijwegt, Rotterdam (NL); Alexander B. Boffa, Oakland, CA (US); John Robert Miller, San Rafael, CA (US)

(73) Assignees: CHEVRON ORONITE TECHNOLOGY B.V., Rotterdam (NL); CHEVRON ORONITE COMPANY LLC, San Ramon, CA (US)

( * ) Notice: Subject to any disclaimer, the term of this patent is extended or adjusted under 35 U.S.C. 154(b) by 135 days.

(21) Appl. No.: 15/333,470

(22) Filed: Oct. 25, 2016

(65) Prior Publication Data

US 2018/0112146 A1 Apr. 26, 2018

(51) Int. Cl.

| | |
|---|---|
| ***C07C 45/50*** | (2006.01) |
| ***C10M 169/06*** | (2006.01) |
| ***C10M 161/00*** | (2006.01) |
| ***F02B 43/10*** | (2006.01) |
| ***C10M 149/16*** | (2006.01) |
| *C10N 20/02* | (2006.01) |
| *C10N 20/04* | (2006.01) |
| *C10N 30/02* | (2006.01) |
| *C10N 30/04* | (2006.01) |
| *C10N 30/10* | (2006.01) |
| *C10N 30/18* | (2006.01) |
| *C10N 30/00* | (2006.01) |
| *C10N 40/25* | (2006.01) |

(52) U.S. Cl.

CPC ........ *C10M 161/00* (2013.01); *C10M 149/16* (2013.01); *F02B 43/10* (2013.01); *C10M 2203/1025* (2013.01); *C10M 2205/024* (2013.01); *C10M 2205/028* (2013.01); *C10M 2207/028* (2013.01); *C10M 2209/084* (2013.01); *C10M 2215/28* (2013.01); *C10M 2217/043* (2013.01); *C10M 2217/06* (2013.01); *C10M 2219/046* (2013.01); *C10M 2223/045* (2013.01); *C10N 2020/02* (2013.01); *C10N 2020/04* (2013.01); *C10N 2030/02* (2013.01); *C10N 2030/04* (2013.01); *C10N 2030/10* (2013.01); *C10N 2030/18* (2013.01); *C10N 2030/42* (2020.05); *C10N 2030/43* (2020.05); *C10N 2030/45* (2020.05); *C10N 2030/78* (2020.05); *C10N 2040/252* (2020.05)

(58) Field of Classification Search

CPC ............ C10M 169/044; C10M 161/00; C10M 149/16; C10M 2205/024; C10M 2209/084; C10M 2215/28; C10M 2203/1025; C10M 2217/043; C10M 2207/028; C10M 2205/028; C10M 2219/046; C10M 2223/045; C10M 2217/06; C10N 2030/04; C10N 2030/10; C10N 2030/42; C10N 2030/43; C10N 2030/45; C10N 2030/78; C10N 2040/252

See application file for complete search history.

(56) References Cited

U.S. PATENT DOCUMENTS

| | | | |
|---|---|---|---|
| 2,551,813 | A | 5/1951 | Pinkney et al. |
| 2,992,708 | A | 7/1961 | Lyon |
| 3,018,291 | A | 1/1962 | Anderson et al. |
| 3,024,237 | A | 3/1962 | Drummond et al. |
| 3,100,673 | A | 8/1963 | Ulmer et al. |
| 3,172,892 | A | 3/1965 | Le Suer et al. |
| 3,219,666 | A | 11/1965 | Norman et al. |
| 3,272,746 | A | 9/1966 | Le Suer et al. |
| 3,361,673 | A | 1/1968 | Stuart et al. |
| 3,381,022 | A | 4/1968 | Le Suer et al. |
| 3,560,455 | A | 2/1971 | Hazen et al. |
| 3,819,660 | A | 6/1974 | Cahill et al. |
| 3,912,764 | A | 10/1975 | Palmer, Jr. |
| 4,152,499 | A | 5/1979 | Boerzel et al. |
| 4,234,435 | A | 11/1980 | Meinhardt et al. |
| 4,240,916 | A | 12/1980 | Rossi |
| 4,605,808 | A | 8/1986 | Samson |
| 5,112,507 | A | 5/1992 | Harrison |
| 5,241,003 | A | 8/1993 | Degonia et al. |
| 5,286,799 | A | 2/1994 | Harrison et al. |
| 5,319,030 | A | 6/1994 | Harrison et al. |
| 5,334,321 | A | 8/1994 | Harrison et al. |
| 5,356,552 | A | 10/1994 | Harrison et al. |
| 5,523,417 | A | 6/1996 | Blackborow et al. |

(Continued)

FOREIGN PATENT DOCUMENTS

| | | |
|---|---|---|
| EP | 0355895 | 2/1990 |
| EP | 0587381 | 3/1994 |

(Continued)

*Primary Examiner* — Prem C Singh
*Assistant Examiner* — Francis C Campanell

(57) ABSTRACT

This invention encompasses lubricating oil compositions comprising a base oil, a biodiesel fuel and a Mannich condensation product. A method for inhibiting viscosity increase in a diesel engine fueled at least in part with a biodiesel fuel is also described.

16 Claims, No Drawings

(56) References Cited

U.S. PATENT DOCUMENTS

| | | | | |
|---|---|---|---|---|
| 5,792,729 | A | 8/1998 | Harrison et al. | |
| 6,030,930 | A | 2/2000 | Emert et al. | |
| 6,156,850 | A | 12/2000 | Harrison et al. | |
| 6,284,716 | B1 | 9/2001 | Gunther et al. | |
| 6,451,920 | B1 | 9/2002 | Harrison et al. | |
| 6,512,055 | B2 | 1/2003 | Gunter et al. | |
| 7,745,541 | B2 | 6/2010 | Ruhe, Jr. et al. | |
| 7,745,542 | B2 | 6/2010 | Ruhe, Jr. et al. | |
| 7,816,309 | B2 | 10/2010 | Stokes et al. | |
| 7,820,604 | B2 | 10/2010 | Ruhe, Jr. et al. | |
| 7,838,474 | B2 | 11/2010 | Boffa | |
| 7,858,566 | B2 | 12/2010 | Ruhe, Jr. et al. | |
| 7,928,044 | B2 | 4/2011 | Stokes et al. | |
| 7,960,322 | B2 | 6/2011 | Boffa | |
| 7,964,002 | B2 | 6/2011 | DeBlase et al. | |
| 7,964,543 | B2 * | 6/2011 | Harrison | C08F 8/32 508/508 |
| 8,067,347 | B2 | 11/2011 | Ruhe, Jr. et al. | |
| 8,394,747 | B2 | 3/2013 | Harrison et al. | |
| 8,455,681 | B2 | 6/2013 | Harrison et al. | |
| 8,680,029 | B2 | 3/2014 | Habeeb et al. | |
| 8,722,927 | B2 | 5/2014 | Harrison et al. | |
| 8,729,297 | B2 | 5/2014 | Harrison et al. | |
| 9,090,849 | B2 | 7/2015 | Adamczewska et al. | |
| 2007/0113467 | A1 | 5/2007 | Abou-Nemeh | |
| 2008/0182768 | A1 | 7/2008 | Devlin et al. | |
| 2009/0111721 | A1 * | 4/2009 | Boffa | C10M 129/10 508/371 |
| 2011/0207642 | A1 | 8/2011 | Strickland et al. | |
| 2015/0033617 | A1 | 2/2015 | Arondel et al. | |
| 2015/0105306 | A1 | 4/2015 | Nelson | |
| 2015/0307803 | A1 | 10/2015 | Zhang | |

FOREIGN PATENT DOCUMENTS

| | | |
|---|---|---|
| EP | 0602863 | 6/1994 |
| EP | 1489281 | 12/2004 |
| EP | 1712605 | 10/2006 |
| EP | 1717300 | 11/2006 |
| EP | 2083024 | 7/2009 |
| EP | 2290041 | 8/2012 |

* cited by examiner

LUBRICATING OIL COMPOSITIONS COMPRISING A BIODIESEL FUEL AND A MANNICH CONDENSATION PRODUCT

FIELD OF THE INVENTION

Provided herein are lubricating oil compositions comprising of a base oil, and a Mannich condensation product, wherein the composition is contaminated with at least 0.3 wt % of a biodiesel fuel or decomposition products thereof. Methods of making and using the lubricating oil compositions are also described. A method of inhibiting viscosity increase in a diesel engine fueled at least in part with biodiesel fuel is described.

BACKGROUND OF THE INVENTION

The contamination or dilution of lubricating engine oils in internal combustion engines such as biodiesel engines has been an industry concern. Biodiesel fuels comprise components of low volatility which are slow to vaporize after injecting into the cylinders of the biodiesel engine. This may result in an accumulation of these components of low volatility on the cylinder wall where they can be subsequently deposited onto the crankshaft by the action of the piston rings. Because biodiesel fuels generally have low oxidative stability, these deposits on the cylinder wall or in the crankshaft can degrade oxidatively and form polymerized and cross-linked biodiesel gums, sludges or varnish-like deposits on the metal surfaces that may damage the biodiesel engine or the crankshaft in addition to increasing the viscosity of the lubricant. Furthermore, biodiesel fuels and resulting partially combusted decomposition products can contaminate the engine's lubricants. These biodiesel contaminants further contribute to oxidization of the engine oil, deposit formation, and corrosion, particularly of lead and copper based bearing material. Therefore, there is a need for improved additives formulations to solve the problem of oxidation, corrosion, deposits, and viscosity increase within the engine.

DESCRIPTION OF RELATED ART

Oil-soluble Mannich condensation products are useful in internal combustion engine lubricating oils. These products generally act as dispersants to disperse sludge, varnish, and lacquer, and prevent the formation of deposits. In general, conventional oil-soluble Mannich condensation products are formed from the reaction of polyisobutyl-substituted phenols with formaldehyde and an amine or a polyamine. For example, U.S. Pat. Nos. 7,964,543; 8,394,747; 8,455,681; 8,722,927 and 8,729,297 and U.S. Patent Application No. 2015/0105306 disclose that 0.01 wt. % to 10.0 wt. % of a Mannich condensation product formed by combining, under reaction conditions, a polyisobutyl-substituted hydroxyaromatic compound wherein the polyisobutyl group is derived from polyisobutene containing at least 50 weight percent methylvinylidene isomer and having a number average molecular weight in the range of about 400 to about 5000, an aldehyde, an amino acid or ester thereof, and an alkali metal base, can be used in an engine lubricating oil composition.

U.S. Pat. Nos. 7,960,322 and 7,838,474, 7,964,002 8,680,029, 9,090,849, U.S. Patent Application Nos. 20070113467, 2008/0182768, 2011/0207642, 2015/0033617, 2015/0307803, and foreign application EP2290041, disclose additive formulations or methods to address oxidation and deposits within the engine due to the influence of biodiesel.

SUMMARY OF THE INVENTION

Provided herein are lubricating oil compositions that can inhibit the viscosity increase of the lubricant. In one aspect, the present invention is directed to a lubricating oil composition contaminated with at least about 0.3 wt % of a biodiesel fuel or a decomposition product thereof, based on the total weight of the lubricating oil composition, comprising a major amount of base oil of lubricating viscosity; and a Mannich condensation product.

In some embodiments, the lubricating oil composition disclosed herein is substantially free of a vegetable oil or animal oil. In other embodiments, the lubricating oil composition disclosed herein is free of a vegetable oil or animal oil.

In certain embodiments, the lubricating oil composition disclosed herein further comprises at least one additive selected from the group consisting of antioxidants, antiwear agents, detergents, rust inhibitors, demulsifiers, friction modifiers, multi-functional additives, viscosity index improvers, pour point depressants, foam inhibitors, metal deactivators, dispersants, corrosion inhibitors, lubricity improvers, thermal stability improvers, anti-haze additives, icing inhibitors, dyes, markers, static dissipaters, biocides and combinations thereof. In other embodiments, the at least one additive is at least one antiwear agent. In further embodiments, the at least one antiwear agent comprises a zinc dialkyl dithiophosphate compound. In still further embodiments, the phosphorous content derived from the zinc dialkyldithiophosphate compound is from about 0.001 wt. % to about 0.5 wt. %, from about 0.01 wt. % to about 0.08 wt. %, or from about 0.01 wt. % to about 0.12 wt. %, based on the total weight of the lubricating oil composition.

In some embodiments, the sulfated ash content of the lubricating oil composition disclosed herein is at most about 2.0, 1.5, 1.0, 0.8, 0.6, or 0.4 wt. %, based on the total weight of the lubricating oil composition.

In certain embodiments, the biodiesel fuel of the lubricating oil composition disclosed herein comprises an alkyl ester of a long chain fatty acid. In further embodiments, the long chain fatty acid comprises from about 12 carbon atoms to about 30 carbon atoms.

In certain embodiments, the amount of the biodiesel fuel is from at least 0.3 wt. %, or from about 0.3 to 20 wt. %, 1 wt. % to about 20 wt. %, 1 wt. % to about 15 wt. %, 1 wt. % to about 10 wt. %, 1 wt. % to about 9 wt. %, 1 wt. % to about 8 wt. %, 1 wt. % to about 7 wt. %, 4 wt. % to about 8 wt. %, or from 1 wt. %, 2 wt. %, 3 wt. %, 4 wt. %, 5 wt. %, 6 wt. %, 7 wt. %, 8 wt. %, or 9 wt. %, based on the total weight of the lubricating oil composition.

In some embodiments, the amount of the base oil of the lubricating oil composition disclosed herein is at least 40 wt. %, based on the total weight of the lubricating oil composition. In further embodiments, the base oil has a kinematic viscosity from about 4 cSt to about 20 cSt at 100° C.

Other embodiments will be in part apparent and in part pointed out hereinafter.

Definitions

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Biofuel" refers to a fuel (e.g., methane) that is produced from renewable biological resources. The renewable biological resources include recently living organisms and their metabolic byproducts (e.g., feces from cows), plants, or biodegradable outputs from industry, agriculture, forestry and households. Examples of biodegradable outputs include straw, timber, manure, rice husks, sewage, biodegradable waste, food leftovers, wood, wood waste, wood liquors, peat, railroad ties, wood sludge, spent sulfite liquors, agricultural waste, straw, tires, fish oils, tall oil, sludge waste, waste alcohol, municipal solid waste, landfill gases, other waste, and ethanol blended into motor gasoline. Plants that can be used to produce biofuels include corn, soybeans, flaxseed, rapeseed, sugar cane, palm oil and jatropha. Examples of biofuel include alcohol derived from fermented sugar and biodiesel derived from vegetable oil or wood.

"Biodiesel fuel" refers to an alkyl ester made from esterification or transesterification of natural oils for use to power diesel engines. In some embodiments, the biodiesel fuel is produced by esterifying a natural oil with an alcohol (e.g., ethanol or methanol) in the presence of a catalyst to form an alkyl ester. In other embodiments, the biodiesel fuel comprises at least one alkyl ester of a long chain fatty acid derived from a natural oil such as vegetable oils or animal fats. In further embodiments, the long chain fatty acid contains from about 8 carbon atoms to about 40 carbon atoms, from about 12 carbon atoms to about 30 carbon atoms, or from about 14 carbon atoms to about 24 carbon atoms. In certain embodiments, the biodiesel fuel disclosed herein is used to power conventional diesel-engines designed to be powered by petroleum diesel fuels. The biodiesel fuel generally is biodegradable and non-toxic, and typically produces about 60% less net carbon dioxide emissions than petroleum-based diesel.

"Petrodiesel fuel" refers to a diesel fuel produced from petroleum.

"A major amount" of a base oil refers to the amount of the base oil is at least 40 wt. % of the lubricating oil composition. In some embodiments, "a major amount" of a base oil refers to an amount of the base oil more than 50 wt. %, more than 60 wt. %, more than 70 wt. %, more than 80 wt. %, or more than 90 wt. % of the lubricating oil composition.

A composition that is "substantially free" of a compound refers to a composition which contains less than 20 wt. %, less than 10 wt. %, less than 5 wt. %, less than 4 wt. %, less than 3 wt. %, less than 2 wt. %, less than 1 wt. %, less than 0.5 wt. %, less than 0.1 wt. %, or less than 0.01 wt. % of the compound, based on the total weight of the composition.

A composition that is "free" of a compound refers to a composition which contains from 0.001 wt. % to 0 wt. % of the compound, based on the total weight of the composition.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

The term "metal" means alkali metals, alkaline earth metals, or mixtures thereof.

The term "alkaline earth metal" refers to calcium, barium, magnesium, and strontium.

The term "alkali metal" refers to lithium, sodium, potassium, rubidium, and cesium.

The term "sulfated ash content" refers to the amount of metal-containing additives (e.g., calcium, magnesium, molybdenum, zinc, etc.) in a lubricating oil composition and is typically measured according to ASTM D874, which is incorporated herein by reference.

The term "Mannich condensation product" as used herein refers to a mixture of products obtained by the condensation reaction of a polyisobutyl-substituted hydroxyaromatic compound with an aldehyde and an amino acid as described herein, to form condensation products having the formulas given below. The formulas given below are provided only as some examples of the Mannich condensation products believed to be of the present invention and are not intended to exclude other possible Mannich condensation products that may be formed using the methods described herein.

Formula 1

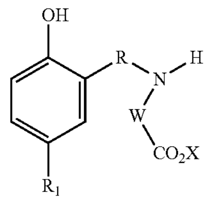

Formula 2

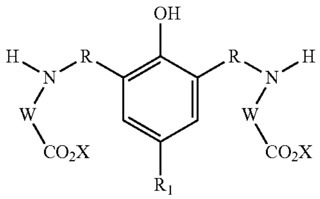

Formula 3

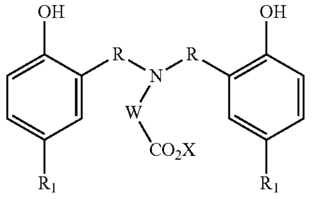

Formula 4

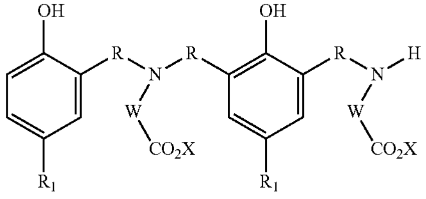

-continued

Formula 5

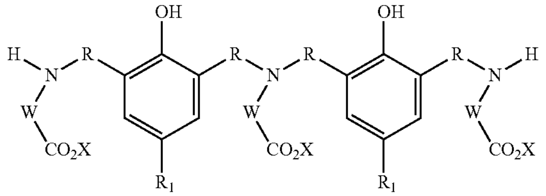

Formula 6

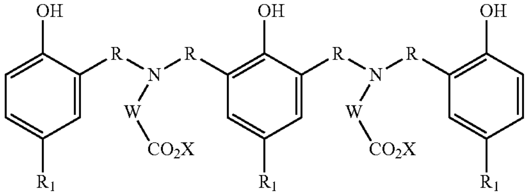

wherein R, $R_1$, X and W are as defined herein.

DETAILED DESCRIPTION OF THE INVENTION

Provided herein are lubricating oil compositions contaminated with at least about 0.3 wt % of a biodiesel fuel or a decomposition product thereof, based on the total weight of the lubricating oil composition, comprising a major amount of base oil of lubricating viscosity; and a Mannich condensation product.

Mannich Condensation Product

In an embodiment, the Mannich condensation product is prepared by the condensation of a polyisobutyl-substituted hydroxyaromatic compound, wherein the polyisobutyl group is derived from polyisobutene containing at least about 70 wt. % methylvinylidene isomer and has a number average molecular weight in the range of from about 400 to about 2,500, an aldehyde, an amino acid or ester derivative thereof, and an alkali metal base. In general, the principal Mannich condensation product can be represented by the structure of formula 7:

Formula 7

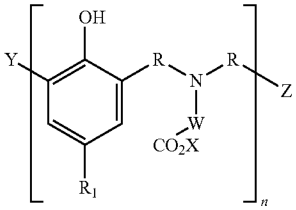 I wherein each R is independently —CHR'—, R' is a branched or linear alkyl having one carbon atom to about 10 carbon atoms, a cycloalkyl having from about 3 carbon atoms to about 10 carbon atoms, an aryl having from about 6 carbon atoms to about 10 carbon atoms, an alkaryl having from about 7 carbon atoms to about 20 carbon atoms, or aralkyl having from about 7 carbon atoms to about 20 carbon atoms, $R_1$ is a polyisobutyl group derived from polyisobutene containing at least about 70 wt. % methylvinylidene isomer and having a number average molecular weight in the range of about 400 to about 2,500;

X is hydrogen, an alkali metal ion or alkyl having one to about 6 carbon atoms;

W is $-[CHR'']-_m$ wherein each R" is independently H, alkyl having one carbon atom to about 15 carbon atoms, or a substituted-alkyl having one carbon atom to about 10 carbon atoms and one or more substituents selected from the group consisting of amino, amido, benzyl, carboxyl, hydroxyl, hydroxyphenyl, imidazolyl, imino, phenyl, sulfide, or thiol; and m is an integer from 1 to 4;

Y is hydrogen, alkyl having one carbon atom to about 10 carbon atoms, —CHR'OH, wherein R' is as defined above, or of formula 8

Formula 8

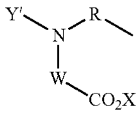

wherein Y' is —CHR'OH, wherein R' is as defined above; and R, X, and W are as defined above;

Z is hydroxyl, a hydroxyphenyl group of formula 9 or 10:

Formula 9

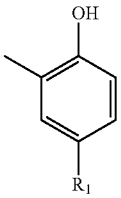

or

Formula 10

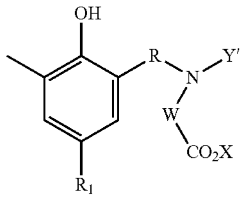

wherein R, $R_1$, Y', X, and W are as defined above, and n is an integer from 0 to 20, with the proviso that when n=0, Z must be of Formula 10 as defined above.

In one embodiment, the $R_1$ polyisobutyl group has a number average molecular weight of about 500 to about 2,500. In one embodiment, the $R_1$ polyisobutyl group has a number average molecular weight of about 700 to about 1,500. In one embodiment, the $R_1$ polyisobutyl group has a number average molecular weight of about 700 to about 1,100. In one embodiment, the $R_1$ polyisobutyl group is derived from polyisobutene containing at least about 70 wt. % methylvinylidene isomer. In one embodiment, the $R_1$ polyisobutyl group is derived from polyisobutene containing at least about 90 wt. % methylvinylidene isomer.

In the compound of formula I above, X is an alkali metal ion and most preferably a sodium or potassium ion. In another embodiment, in the compound of formula I above, X is alkyl selected from methyl or ethyl.

In one embodiment, R is $CH_2$, $R_1$ is derived from polyisobutene containing at least about 70 wt. % methylvinylidene isomer and a number average molecular weight in the range of about 700 to about 1,100, W is $CH_2$, X is sodium ion and n is 0 to 20.

The Mannich condensation products for use in the lubricating oil composition of the present invention can be prepared by combining under reaction conditions a polyisobutyl-substituted hydroxyaromatic compound, wherein the polyisobutyl group has a number average molecular weight in the range of from about 400 to about 2,500, an aldehyde, an amino acid or ester derivative thereof, and an alkali metal base. In one embodiment, Mannich condensation product prepared by the Mannich condensation of:

(a) a polyisobutyl-substituted hydroxyaromatic compound having the formula 11:

Formula 11

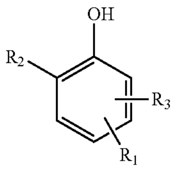

wherein $R_1$ is a polyisobutyl group derived from polyisobutene containing at least about 70 wt. % methylvinylidene isomer and having a number average molecular weight in the range of about 400 to about 2,500, $R_2$ is hydrogen or lower alkyl having one carbon atom to about 10 carbon atoms, and $R_3$ is hydrogen or —OH;

(b) a formaldehyde or an aldehyde having the formula 12:

Formula 12

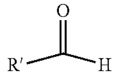

wherein R' is branched or linear alkyl having one carbon atom to about 10 carbon atoms, cycloalkyl having from about 3 carbon atoms to about 10 carbon atoms, aryl having from about 6 carbon atoms to about 10 carbon atoms, alkaryl having from about 7 carbon atoms to about 20 carbon atoms, or aralkyl having from about 7 carbon atoms to about 20 carbon atoms;

(c) an amino acid or ester derivative thereof having the formula 13:

Formula 13

wherein W is $—[CHR'']—_m$ wherein each R" is independently H, alkyl having one carbon atom to about 15 carbon atoms, or a substituted-alkyl having one carbon atom to about 10 carbon atoms and one or more substituents selected from the group consisting of amino, amido, benzyl, carboxyl, hydroxyl, hydroxyphenyl, imidazolyl, imino, phenyl, sulfide, or thiol; and m is an integer from one to 4, and A is hydrogen or alkyl having one carbon atom to about 6 carbon atoms; and (d) an alkali metal base.

Polyisobutyl-Substituted Hydroxyaromatic Compound

A variety of polyisobutyl-substituted hydroxyaromatic compounds can be utilized in the preparation of the Mannich condensation products of this invention. The critical feature is that the polyisobutyl substituent be large enough to impart oil solubility to the finished Mannich condensation product. In general, the number of carbon atoms on the polyisobutyl substituent group that are required to allow for oil solubility of the Mannich condensation product is on the order of about $C_{20}$ and higher. This corresponds to a molecular weight in the range of about 400 to about 2,500. It is desirable that the $C_{20}$ or higher alkyl substituent on the phenol ring be located in the position para to the OH group on the phenol.

The polyisobutyl-substituted hydroxyaromatic compound is typically a polyisobutyl-substituted phenol wherein the polyisobutyl moiety is derived from polyisobutene containing at least about 70 wt. % methylvinylidene isomer and more preferably the polyisobutyl moiety is derived from polyisobutene containing at least about 80 wt. %, or at least about 90 wt. % methylvinylidene isomer. The term "polyisobutyl or polyisobutyl substituent" as used herein refers to the polyisobutyl substituent on the hydroxyaromatic ring. The polyisobutyl substituent has a number average molecular weight in the range of about 400 to about 2,500. In one embodiment, the polyisobutyl moiety has a number average molecular weight in the range of about 450 to about 2,500. In one embodiment, the polyisobutyl moiety has a number average molecular weight in the range of about 700 to about 1,500. In one embodiment, the polyisobutyl moiety has a number average molecular weight in the range of about 700 to about 1,100. In one embodiment, the polyisobutyl moiety has a number average molecular weight in the range of about 900 to about 1,100.

In one preferred embodiment, the attachment of the polyisobutyl substituent to the hydroxyaromatic ring is para to the hydroxyl moiety in at least about 60 percent of the total polyisobutyl-substituted phenol molecules. In one embodiment, the attachment of the polyisobutyl substituent to the hydroxyaromatic ring is para to the hydroxyl moiety in at least about 70 percent of the total polyisobutyl-substituted phenol molecules. In one embodiment, the attachment of the polyisobutyl substituent to the hydroxyaromatic ring is para to the hydroxyl moiety in at least about 80 percent of the total polyisobutyl-substituted phenol molecules. In one embodiment, the attachment of the polyisobutyl substituent to the hydroxyaromatic ring is para to the hydroxyl moiety on the phenol ring in at least about 90 percent of the total polyisobutyl-substituted phenol molecules.

Di-substituted phenols are also suitable starting materials for the Mannich condensation products of this invention. Di-substituted phenols are suitable provided that they are substituted in such a way that there is an unsubstituted ortho position on the phenol ring. Examples of suitable di-substituted phenols are o-cresol derivatives substituted in the para position with a $C_{20}$ or greater polyisobutyl substituent and the like.

In one embodiment, a polyisobutyl-substituted phenol has the following formula 14:

Formula 14

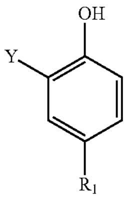

wherein $R_1$ is polyisobutyl group derived from polyisobutene containing at least about 70 wt. % methylvinylidene isomer and having a number average molecular weight in the range of about 400 to about 2,500, and Y is hydrogen.

Suitable polyisobutenes may be prepared using boron trifluoride ($BF_3$) alkylation catalyst as described in U.S. Pat. Nos. 4,152,499 and 4,605,808, the contents of each of these references being incorporated herein by reference. Commercially available polyisobutenes having a high alkylvinylidene content include Glissopal® 1000, 1300 and 2300, available from BASF.

The preferred polyisobutyl-substituted phenol for use in the preparation of the Mannich condensation products is a mono-substituted phenol, wherein the polyisobutyl substituent is attached at the para-position to the phenol ring. However, other polyisobutyl-substituted phenols that may undergo the Mannich condensation reaction may also be used for preparation of the Mannich condensation products according to the present invention.

Solvent

Solvents may be employed to facilitate handling and reaction of the polyisobutyl-substituted phenols in the preparation of the Mannich condensation products. Examples of suitable solvents are hydrocarbon compounds such as heptane, benzene, toluene, chlorobenzene, aromatic solvent, neutral oil of lubricating viscosity, paraffins and naphthenes. Examples of other commercially available suitable solvents that are aromatic mixtures include Chevron® Aromatic 100N, neutral oil, Exxon® 150N, neutral oil.

In one embodiment, the Mannich condensation product may be first dissolved in an alkyl-substituted aromatic solvent. Generally, the alkyl substituent on the aromatic solvent has from about 3 carbon atoms to about 15 carbon atoms. In one embodiment, the alkyl substituent on the aromatic solvent has from about 6 carbon atoms to about 12 carbon atoms.

Aldehydes

Suitable aldehydes for use in forming the Mannich condensation product include formaldehyde or aldehydes having the formula 12:

Formula 12

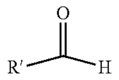

wherein R' is branched or linear alkyl having from one carbon atom to about 10 carbon atoms, cycloalkyl having from about 3 carbon atoms to about 10 carbon atoms, aryl having from about 6 carbon atoms to about 10 carbon atoms, alkaryl having from about 7 carbon atoms to about 20 carbon atoms, or aralkyl having from about 7 carbon atoms to about 20 carbon atoms.

Representative aldehydes include, but are not limited to, aliphatic aldehydes such as formaldehyde, acetaldehyde, propionaldehyde, butyraldehyde, valeraldehyde, caproaldehyde and heptaldehyde. Aromatic aldehydes are also contemplated for use in the preparation of the Mannich condensation products, such as benzaldehyde and alkylbenzaldehyde, e.g., para-tolualdehyde. Also useful are formaldehyde producing reagents, such as paraformaldehyde and aqueous formaldehyde solutions such as formalin. In one preferred embodiment, an aldehyde for use in the in the preparation of the Mannich condensation products is formaldehyde or formalin. By formaldehyde is meant all its forms, including gaseous, liquid and solid. Examples of gaseous formaldehyde is the monomer $CH_2O$ and the trimer, $(CH_2O)_3$ (trioxane) having the formula 15 given below.

Formula 15

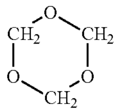

Examples of liquid formaldehyde are the following:

Monomer $CH_2O$ in ethyl ether.

Monomer $CH_2O$ in water which has the formulas $CH_2(H_2O)_2$ (methylene glycol) and $HO(—CH_2O)_n—H$.

Monomer $CH_2O$ in methanol which has the formulas $OHCH_2OCH_3$ and $CH_3O(—CH_2O)_n—H$.

Formaldehyde solutions are commercially available in water and various alcohols. In water it is available as a 37%-50% solution. Formalin is a 37% solution in water. Formaldehyde is also commercially available as linear and cyclic (trioxane) polymers. Linear polymers may be low molecular weight or high molecular weight polymers.

Amino Acid

Suitable amino acids or ester derivatives thereof for use in forming the Mannich condensation product include amino acids having the formula 13:

Formula 13

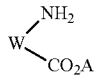

wherein W is $—[CHR'']_m—$, wherein each R'' is independently H, alkyl having one carbon atom to about 15 carbon atoms, or a substituted-alkyl having one carbon atom to about 10 carbon atoms and one or more substituents selected from the group consisting of amino, amido, benzyl, carboxyl, hydroxyl, hydroxyphenyl, imidazolyl, imino, phenyl, sulfide, or thiol; and m is an integer from one to 4, and A is hydrogen or alkyl having one carbon atom to about 6 carbon atoms. Preferably the alkyl is methyl or ethyl.

In one embodiment, the amino acid is glycine.

The term "amino acid salt" as used herein refers to salts of amino acids having the formula 16:

Formula 16

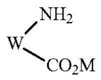

wherein W is as defined above and M is an alkali metal ion. Preferably M is a sodium ion or a potassium ion. More preferably X is a sodium ion.

Some examples of alpha amino acids contemplated for use in the preparation of the Mannich condensation product are given below in Table 1.

TABLE 1
| Name | Formula | Log $K^{25° C., 0\ ionic\ strength}$ |
|---|---|---|
| Alanine | 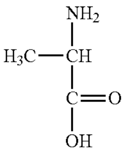 | 9.87 |
| Arigine | 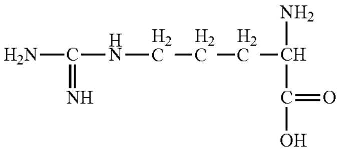 [SMILES: N=C(N)NCCCC(N)C(=O)O] | 8.99 |
| Asparagine | 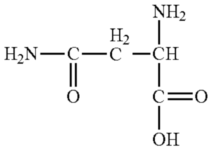 | 8.72 * |
| Aspartic Acid | 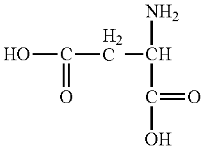 | 10.0 |
| Cysteine | 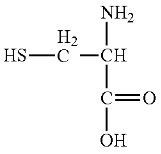 | 10.77 |
| Cystine | 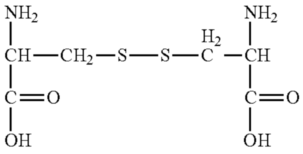 [SMILES: NC(CSSCC(N)C(=O)O)C(=O)O] | 8.80 ** |
| Glutamic Acid | 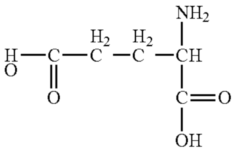 | 9.95 |
| Glutamine | 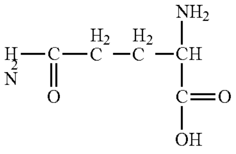 | 9.01 * |
| Glycine | 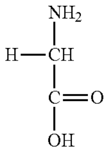 | 9.78 |

TABLE 1-continued
| Name | Formula | Log $K^{25° C., 0\ ionic\ strength}$ |
|---|---|---|
| Histidine | 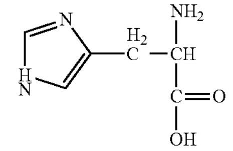 [SMILES: NC(Cc1c[nH]cn1)C(=O)O] | 9.08 * |
| Hydroxylysine | 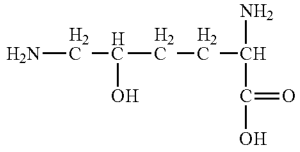 [SMILES: NCC(O)CCC(N)C(=O)O] | |
| Isoleucine | 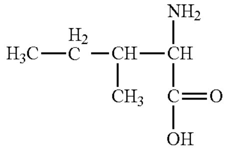 | 9.75 |
| Leucine | 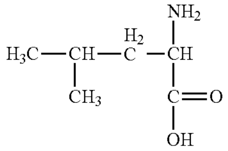 | 9.75 |
| Lysine | 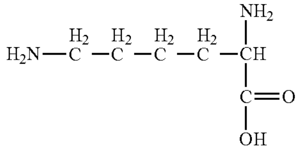 | 10.69 * |
| Methionine | 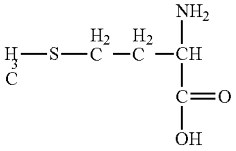 | 9.05 |
| Phenylalanine | 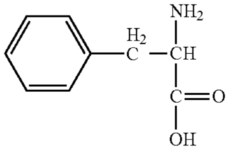 [SMILES: NC(Cc1ccccc1)C(=O)O] | 9.31 |
| Serine | 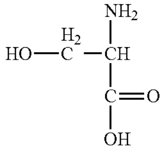 | 9.21 |
| Threonine | 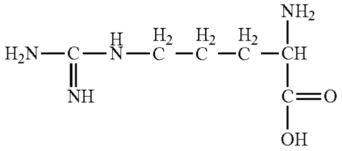 [SMILES: N=C(N)NCCCC(N)C(=O)O] | 9.10 |

TABLE 1-continued

| Name | Formula | Log $K^{25° C., 0\ ionic\ strength}$ |
| --- | --- | --- |
| Tyrosine | 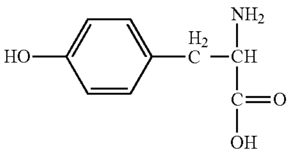 [SMILES: NC(Cc1ccc(O)cc1)C(=O)O] | 10.47 |
| Valine | 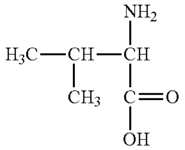 | 9.72 |

* 0.1 ionic strenght.

** 20° C. and 0.1 ionic strength.

Alkali Metal Base

Suitable alkali metal base for use in forming the Mannich condensation product include alkali metal hydroxides, alkali metal alkoxides and the like. In one embodiment, the alkali metal base is an alkali metal hydroxide selected from the group consisting of sodium hydroxide, lithium hydroxide or potassium hydroxide.

In one embodiment, the amino acid may be added in the form of its alkali metal ion salt. In one embodiment, the alkali metal ion is a sodium ion or a potassium ion. In one preferred embodiment, the alkali metal ion is a sodium ion.

General Procedure for Preparation of Mannich Condensation Product

The reaction to form the Mannich condensation products can be carried out batch wise, or in continuous or semi-continuous mode. Normally the pressure for this reaction is atmospheric, but the reaction may be carried out under sub atmospheric or super atmospheric pressure if desired.

The temperature for this reaction may vary widely. The temperature range for this reaction can vary from about 10° C. to about 200° C., or from about 50° C. to about 150° C., or from about 70° C. to about 130° C.

The reaction may be carried out in the presence of a diluent or a mixture of diluents. It is important to ensure that the reactants come into intimate contact with each other in order for them to react. This is an important consideration because the starting materials for the Mannich condensation products include the relatively non polar polyisobutyl-substituted hydroxyl aromatic compounds and the relatively polar amino acid or ester derivative thereof. It is therefore necessary to find a suitable set of reaction conditions or diluents that will dissolve all the starting materials.

Diluents for this reaction must be capable of dissolving the starting materials of this reaction and allowing the reacting materials to come in contact with each other. Mixtures of diluents can be used for this reaction. Useful diluents for this reaction include water, alcohols, (including methanol, ethanol, isopropanol, 1-propanol, 1-butanol, isobutanol, sec-butanol, butanediol, 2-ethylhexanol, 1-pentanol, 1-hexanol, ethylene glycol, and the like), DMSO, NMP, HMPA, cellosolve, diglyme, various ethers (including diethyl ether, THF, diphenylether, dioxane, and the like), aromatic diluents (including toluene, benzene, o-xylene, m-xylene, p-xylene, mesitylene and the like), esters, alkanes (including pentane, hexane, heptane, octane, and the like), and various natural and synthetic diluent oils (including 100 neutral oils, 150 neutral oils, polyalphaolefins, Fischer-Tropsch derived base oil and the like, and mixtures of these diluents. Mixtures of diluents that form two phases such as methanol and heptane are suitable diluents for this reaction.

The reaction may be carried out by first reacting the hydroxyaromatic compound with the alkali metal base, followed by the addition of the amino acid or ester derivative thereof and the aldehyde, or the amino acid or ester derivative thereof may be reacted with the aldehyde followed by the addition of the hydroxyaromatic compound and the alkali metal base, etc.

It is believed that the reaction of the amino acid, such as glycine, or ester derivative thereof, plus the aldehyde, such as formaldehyde, may produce the intermediate formula

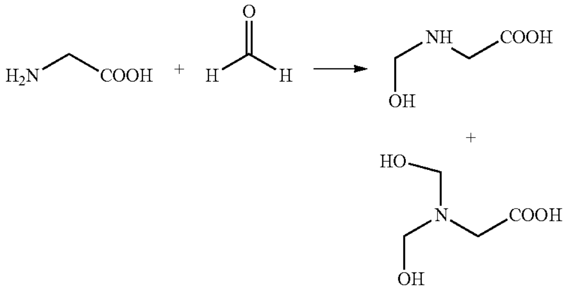

which may ultimately form the cyclic formula 17:

Formula 17

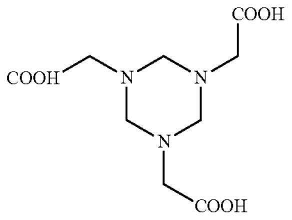

It is believed that these intermediates may react with the hydroxyaromatic compound and the base to form the Mannich condensation products of the present invention.

Alternatively, it is believed that the reaction of the hydroxyaromatic compound with the aldehyde may produce the intermediate formula 18:

Formula 12

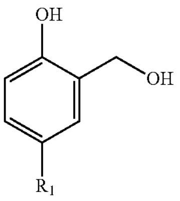

It is also believed that this intermediate may react with the amino acid or ester derivative thereof and the base to form the Mannich condensation product of the present invention.

different formulae that can arise if different charge mole ratios are used. At a minimum the oil-soluble Mannich condensation products should preferable contain at least one polyisobutyl-substituted phenol ring and one amino acid group connected by one aldehyde group and one alkali metal. The polyisobutyl-substituted phenol/aldehyde/amino acid/base charge mole ratio for this molecule, also shown in Table 2 below, is 1.0:1.0:1.0:1.0. Other charge mole ratios are possible and the use of other charge mole ratios can lead to the production of different molecules of different formulas.

TABLE 2

| Product | Polyisobutyl-substituted phenol:aldehyde:amino acid:base (CMR) |
|---|---|
| 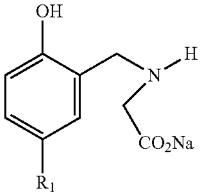 | 1.0:1.0:1.0:1.0 |
| 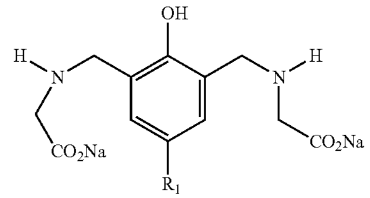 | 1.0:2.0:2.0:2.0 |
| 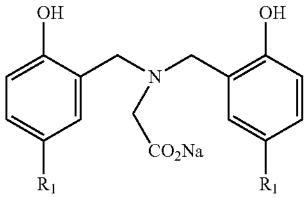 | 2.0:2.0:1.0:1.0 |
| 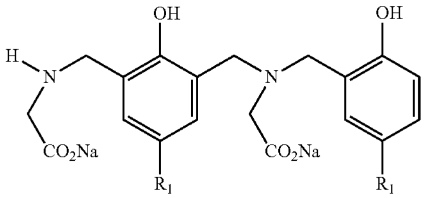 | 2.0:3.0:2.0:2.0 |
| 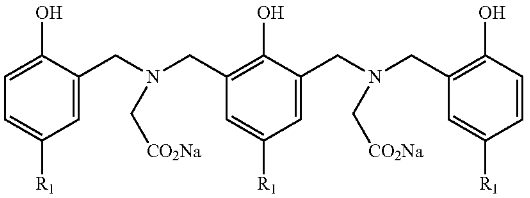 | 3.0:4.0:2.0:2.0 |

The time of the reaction can vary widely depending on the temperature. The reaction time can vary between about 0.1 hour to about 20 hours, or from about 2 hours to about 10 hours, or from about 3 hours to about 7 hours.

The charge mole ratio (CMR) of the reagents can also vary over a wide range. Table 2 below gives a listing of the In one embodiment, the composition further comprises a dispersant.

In one embodiment, the dispersant is a polysuccinimide dispersant. In one embodiment, the polysuccinimide dispersant is a succinimide dispersant derived from terpolymer PIBSA. In one embodiment, the polysuccinimide dispersant is a polysuccinimide dispersant derived from Terpolymer PIBSA, N-phenylenediamine and a polyether amine.

In one embodiment, the dispersant is a borated succinimide dispersant. In one embodiment, the borated dispersant is one derived from the reaction product of a polyisobutenylsuccinic anhydride with a polyamine. Preferably, the borated dispersant is derived from polybutenes having a molecular weight of from 1200 to 1400, most preferably about 1300. The lubricating oil of this invention may comprise greater than 0 to about 6% borated dispersant Preferred lubricating oils of this invention may comprise about 1% to about 5% borated dispersant. Most preferred lubricating oils of this invention may comprise about 1% to about 4% borated dispersant.

In one embodiment, the dispersant is an ethylene carbonate (EC) post-treated succinimide dispersant. The EC-treated dispersant is a polybutene succinimide derived from polybutenes having a molecular weight of at least 1800, preferably from 2000 to 2400. The EC-treated succinimide of this invention is described in U.S. Pat. Nos. 5,334,321 and 5,356,552. The lubricating oil of this invention may comprise greater than 0 to about 10% EC-treated dispersant. Preferred lubricating oils of this invention may comprise about 2% to about 9% EC-treated dispersant. Most preferred lubricating oils of this invention may comprise about 4% to about 8% EC-treated dispersant.

A. The Oil of Lubricating Viscosity

The neutral oil may be selected from Group I base stock, Group II base stock, Group III base stock, Group IV or poly-alpha-olefins (PAO), Group V, or base oil blends thereof. The base stock or base stock blend preferably has a saturate content of at least 65%, more preferably at least 75%; a sulfur content of less than 1%, preferably less than 0.6%, by weight; and a viscosity index of at least 85, preferably at least 100.

In some embodiments, the base oil has a kinematic viscosity of from about 4 cSt to about 20 cSt at 100° C.

These base stocks can be defined as follows:

Group I: base stocks containing less than 90% saturates and/or greater than 0.03% sulfur and having a viscosity index greater than or equal to 80 and less than 120 using test methods specified in the American Petroleum Institute (API) publication "Engine Oil Licensing and Certification Sheet" Industry Services Department, 14th Ed., December 1996, Addendum I, December 1998;

Group II: base stocks containing greater than or equal to 90% saturates and/or greater than 0.03% sulfur and having a viscosity index greater than or equal to 80 and less than 120;

Group III: base stocks which are less than or equal to 0.03% sulfur, greater than or equal to 90% saturates, and greater than or equal to 120.

Group IV: base stocks which comprise PAO's.

Group V: base stocks include all other base stocks not included in Group I, II, III, or IV.

For these definitions, saturates level can be determined by ASTM D 2007, the viscosity index can be determined by ASTM D 2270; and sulfur content by any one of ASTM D 2622, ASTM D 4294, ASTM D 4927, or ASTM D 3120.

B. Biodiesel Fuel

The lubricating oil compositions disclosed herein generally comprise at least one biodiesel fuel. Any biodiesel fuel which can be used to power a diesel-engine in its unaltered form can be used herein. Some non-limiting examples of biodiesel fuels are disclosed in the book by Gerhard Knothe and Jon Van Gerpen, "*The Biodiesel Handbook*," AOCS Publishing, (2005), which is incorporated herein by reference.

In some embodiments, the biodiesel fuel comprises one or more mono-alkyl esters of long chain fatty acids derived from a natural oil such as vegetable oils or animal fats. In other embodiments, the biodiesel fuel comprises one or more of methyl esters of long chain fatty acids. In further embodiments, the number of carbon atoms in the long chain fatty acids is from about 10 to about 30, from about 12 to about 30, from about 14 to about 26, or from about 16 to about 22. In further embodiments, the long chain fatty acid comprises palmitic acid (C16), oleic acid (C18:1), linoleic acid (C18:2) and other acids. In still further embodiments, the biodiesel fuel is derived from esterification or transesterification of corn oil, cashew oil, oat oil, lupine oil, kenaf oil, calendula oil, cotton oil, hemp oil, soybean oil, coffee oil, linseed oil, hazelnut oil, euphorbia oil, pumpkin seed oil, coriander oil, mustard seed oil, camelina oil, sesame oil, safflower oil, rice oil, tung oil, sunflower oil, cocoa oil, peanut oil, opium poppy oil, rapeseed oil, olive oil, castor bean oil, pecan nut oil, jojoba oil, jatropha oil, macadamia nut oil, Brazil nut oil, avocado oil, coconut oil, palm oil, Chinese tallow oil, or algae oil. In still further embodiments, the biodiesel fuel is chemically converted from natural oils or rapeseed, soya, jatropha or other virgin biomass, UCO (used-cooking oil), MSW (municipal solid waste) or from any viable fuel stock.

In certain embodiments, the biodiesel fuel disclosed herein comprises a biodiesel fuel that meets the EN 14214 standard, which is incorporated herein by reference. In other embodiments, the biodiesel fuels disclosed herein meet some of the EN 14214 specifications as shown in Table 3.

TABLE 3

| Property | Units | Lower Limit | Upper Limit | Test-Method |
|---|---|---|---|---|
| Ester content | % | 96.5 | | EN 14103d |
| Density at 15° C. | kg/m$^3$ | 860 | | EN ISO 3675 or EN ISO 12185. |
| Viscosity at 40° C. | mm$^2$/s | 3.5 | — | EN ISO 3104 |
| Flash point | ° C. | >101 | 900 | ISO CD 3679e |
| Sulfur content | mg/kg | — | 5.0 | — |
| Tar remnant (at 10% distillation remnant) | % | — | — | EN ISO 10370 |
| Cetane number | — | 51.0 | 10 | EN ISO 5165 |
| Sulfated ash content | % | — | 0.3 | ISO 3987 |

Generally, a pure biodiesel fuel that meets the ASTM D 6751-03 specifications has a B100 designation. The ASTM D 6751-03 is incorporated herein by reference. In some embodiments, a B100 biodiesel fuel can be mixed with a petroleum diesel fuel to form a biodiesel blend which may reduce emissions and improve engine performance. The biodiesel blend may have a designation "Bxx" wherein xx refers to the amount of the B100 biodiesel in vol. %, based on the total volume of the biodiesel blend. For example, "B6" refers to a biodiesel blend which comprises 6 vol. % of the B100 biodiesel fuel and 94 vol. % of the petroleum diesel fuel.

In some embodiments, the biodiesel fuel disclosed herein is a B100, B95, B90, B85, B80, B75, B70, B65, B60, B55, B50, B45, B40, B35, B30, B25, B20, B15, B10, B8, B6, B5, B4, B3, B2 or B1 biodiesel fuel. In other embodiments, a B100 biodiesel fuel is blended with one or more mineral diesels wherein the amount of the B100 biodiesel fuel is about 5 vol. %, about 6 vol. %, about 10 vol. %, about 15 vol. %, about 20 vol. %, about 25 vol. %, about 30 vol. %, about 35 vol. %, about 40 vol. %, about 45 vol. %, about 50 vol. %, about 55 vol. %, about 60 vol. %, about 65 vol. %, about 70 vol. %, about 75 vol. %, about 80 vol. %, about 85 vol. %, about 90 vol. %, or about 95 vol. %, based on the total volume of the biodiesel blend.

In some embodiments, the biodiesel fuel is used to power conventional diesel-engines designed to be powered by petroleum diesel fuels. In other embodiments, the biodiesel fuel is used to power modified diesel engines designed to be powered by natural oils or other biofuels.

The amount of the biodiesel fuel in the lubricating oil composition can be in any amount suitable to obtain desirable properties such as biodegradability and viscosity. In some embodiments, the amount of the biodiesel fuel in the lubricating oil composition is at least about 0.3 wt. %, is at least about 1 wt. %, at least about 2 wt. %, at least about 3 wt. %, at least about 4 wt. %, at least about 5 wt. %, at least about 10 wt. %, at least about 15 wt. %, at least about 20 wt. %, at least about 25 wt. %, at least about 30 wt. %, at least about 35 wt. %, at least about 40 wt. %, at least about 45 wt. %, or at least about 50 wt. %, or from 0.3 wt. % to at about 20 wt. %, based on the total weight of the lubricating oil composition.

C. Lubricating Oil Additives

In addition to the Mannich condensation products described herein, the lubricating oil composition can comprise additional lubricating oil additives.

Additional Lubricating Oil Additives

The lubricating oil compositions of the present disclosure may also contain other conventional additives that can impart or improve any desirable property of the lubricating oil composition in which these additives are dispersed or dissolved. Any additive known to a person of ordinary skill in the art may be used in the lubricating oil compositions disclosed herein. Some suitable additives have been described in Mortier et al., "Chemistry and Technology of Lubricants", 2nd Edition, London, Springer, (1996); and Leslie R. Rudnick, "Lubricant Additives: Chemistry and Applications", New York, Marcel Dekker (2003), both of which are incorporated herein by reference. For example, the lubricating oil compositions can be blended with additional antioxidants, anti-wear agents, detergents such as metal detergents, rust inhibitors, dehazing agents, demulsifying agents, metal deactivating agents, friction modifiers, pour point depressants, antifoaming agents, co-solvents, corrosion-inhibitors, ashless dispersants, multifunctional agents, dyes, extreme pressure agents and the like and mixtures thereof. A variety of the additives are known and commercially available. These additives, or their analogous compounds, can be employed for the preparation of the lubricating oil compositions of the disclosure by the usual blending procedures.

In the preparation of lubricating oil formulations it is common practice to introduce the additives in the form of 10 to 80 wt. % active ingredient concentrates in hydrocarbon oil, e.g. mineral lubricating oil, or other suitable solvent.

Usually these concentrates may be diluted with 3 to 100, e.g., 5 to 40, parts by weight of lubricating oil per part by weight of the additive package in forming finished lubricants, e.g. crankcase motor oils. The purpose of concentrates, of course, is to make the handling of the various materials less difficult and awkward as well as to facilitate solution or dispersion in the final blend.

D. Processes of Preparing Lubricating Oil Compositions

The lubricating oil compositions disclosed herein can be prepared by any method known to a person of ordinary skill in the art for making lubricating oils. In some embodiments, the base oil can be blended or mixed with a Mannich condensation product. Optionally, one or more other additives in additional to the Mannich condensation product can be added. The Mannich condensation product and the optional additives may be added to the base oil individually or simultaneously. In some embodiments, the Mannich condensation product and the optional additives are added to the base oil individually in one or more additions and the additions may be in any order. In other embodiments, the Mannich condensation product and the additives are added to the base oil simultaneously, optionally in the form of an additive concentrate. In some embodiments, the solubilizing of the Mannich condensation product or any solid additives in the base oil may be assisted by heating the mixture to a temperature from about 25° C. to about 200° C., from about 50° C. to about 150° C. or from about 75° C. to about 125° C.

Any mixing or dispersing equipment known to a person of ordinary skill in the art may be used for blending, mixing or solubilizing the ingredients. The blending, mixing or solubilizing may be carried out with a blender, an agitator, a disperser, a mixer (e.g., planetary mixers and double planetary mixers), a homogenizer (e.g., Gaulin homogenizers and Rannie homogenizers), a mill (e.g., colloid mill, ball mill and sand mill) or any other mixing or dispersing equipment known in the art.

E. Application of the Lubricating Oil Compositions

The lubricating oil composition disclosed herein may be suitable for use as motor oils (that is, engine oils or crankcase oils), in a diesel engine, particularly a diesel engine fueled at least in part with a biodiesel fuel.

The lubricating oil composition of the present invention may, also be used to prevent or inhibit viscosity increase of the lubricant, cool hot engine parts, keep the engine free of rust and deposits, and seal the rings and valves against leakage of combustion gases. The motor oil composition may comprise a base oil, a polysuccinimide dispersant disclosed herein, and may be contaminated with a biodiesel fuel. Optionally, the motor oil composition may further comprises one or more other additives in addition to the polysuccinimide dispersant. In some embodiments, the motor oil composition further comprises a pour point depressant, a viscosity index improver, a detergent, additional dispersant(s), an anti-wear, an antioxidant, a friction modifier, a rust inhibitor, or a combination thereof.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

EXAMPLES

The following examples are intended for illustrative purposes only and do not limit in any way the scope of the present invention.

Examples 1-11 and Comparative Examples 1-4 were top-treated with 7 wt. % B100 biodiesel fuel to simulate the effects of fuel dilution in biodiesel-fueled engines.

Baseline Formulation

A base-line formulation was prepared and used for assessing the performance of various dispersants in the CEC-L-

109 bench test. The base-line formulation contained a mixture of calcium sulfonate and phenate detergents, zinc dialkyldithiophosphate, an antioxidant mixture, 0.3 wt. % of a polyacrylate pour point depressant (available from Evonik Rohmax), 5 ppm Si of a foam inhibitor, and 6.8 wt. % non-dispersant type styrene isoprene copolymer viscosity index improver concentrate (available from Infineum under the designation “SV 201”) in a base oil which was a mixture of a group III hydroisomerized base stock Nexbase® 3043 (18 wt. %, available from Neste) and a group III hydroisomerized base stock Nexbase® 3050 Group III base oil (82 wt. %, available from Neste). The composition had a phosphorus content of 0.074 wt. %, sulfur content of 0.191 wt. %, and sulfated ash of 0.77 wt %.

Mannich Condensation Product of the Examples

The Mannich condensation product of the following examples is a reaction product of a polyisobutyl-substituted phenol (prepared with a 1000 number average MW PIB having greater than 70 wt. % methylvinylidene isomer), sodium glycine, and formaldehyde). For methods of making and using said Mannich dispersant please refer to U.S. Pat. Nos. 7,964,543; 8,394,747; 8,455,681; 8,722,927 and 8,729,297, their entireties incorporated herein by reference.

Polysuccinimide Dispersant of the Examples

The polysuccinimide dispersant of the following examples is a non-conventional polysuccinimide dispersant derived from Terpolymer PIBSA (2300 number average MW PIB having greater than 70 wt. % methylvinylidene isomer), N-phenylenediamine and a polyether amine known as Huntsman Jeffamine® XTJ-501 (also called ED-900). For methods of making said polysuccinimide dispersant please refer to U.S. Pat. No. 7,745,541, the entirety of which is incorporated herein by reference.

Ethylene Carbonate Dispersant of the Examples

The EC-treated dispersant is a polybutene bis-succinimide derived from polybutenes having a molecular weight of about 2300.

Borated Bissuccinimide of the Examples

The borated bis-succinimide dispersant is derived from polybutenes having a molecular weight of about 1300.

Example 1

A lubricating oil composition was prepared consisting of the baseline formulation above with the addition of a Mannich condensation product with 3.3 wt. % actives.

Example 2

A lubricating oil composition was prepared consisting of the baseline formulation above with the addition of a Mannich condensation product with 4.4 wt. % actives.

Example 3

A lubricating oil composition was prepared consisting of the baseline formulation above with the addition of a Mannich condensation product with 0.83 wt. % actives and an ethylene carbonate post-treated polyisobutenyl succinimide with 2.28 wt. % actives.

Example 4

A lubricating oil composition was prepared consisting of the baseline formulation above with the addition of a Mannich condensation product with 0.55 wt. % actives and an ethylene carbonate post-treated polyisobutenyl succinimide with 3.42 wt. % actives.

Example 5

A lubricating oil composition was prepared consisting of the baseline formulation above with the addition of a Mannich condensation product with 0.83 wt. % actives and an ethylene carbonate post-treated polyisobutenyl succinimide with 3.14 wt. % actives.

Example 6

A lubricating oil composition was prepared consisting of the baseline formulation above with the addition of a Mannich condensation product with 1.65 wt. % actives and an ethylene carbonate post-treated polyisobutenyl succinimide with 2.28 wt. % actives.

Example 7

A lubricating oil composition was prepared consisting of the baseline formulation above with the addition of Mannich condensation product with 2.2 wt. % actives and an ethylene carbonate post-treated polyisobutenyl succinimide with 1.71 wt. % actives.

Example 8

A lubricating oil composition was prepared consisting of the baseline formulation above with the addition of a Mannich condensation product with 1.65 wt. % actives and a polysuccinimide dispersant with 2.36 wt. % actives.

Example 9

A lubricating oil composition was prepared consisting of the baseline formulation above with the addition of a Mannich condensation product with 0.83 wt. % actives and a borated bissuccinimide with 2.52 wt. % actives.

Comparative Example 1

A lubricating oil composition was prepared consisting of the baseline formulation above with the addition of an ethylene carbonate post-treated polyisobutenyl bissuccinimide having 2.28 wt. % actives.

Comparative Example 2

A lubricating oil composition was prepared consisting of the baseline formulation above with the addition of an ethylene carbonate post-treated polyisobutenyl bissuccinimide having 4.56 wt. % actives.

Comparative Example 3

A lubricating oil composition was prepared consisting of the baseline formulation above with the addition of a borated bissuccinimide having 2.52 wt. % actives.

Comparative Example 4

A lubricating oil composition was prepared consisting of the baseline formulation above with the addition of a borated bissuccinimide having 5.04 wt. % actives.

Oxidation Test for Engine Oils Operating in the Presence of Biodiesel Fuel: CEC L-109-14

Oxidation Test for Engine Oils Operating in the Presence of Biodiesel Fuel is a standard test method for evaluation of viscosity increase and oxidation level of an aged oil in the presence of biodiesel. The test is conducted at 150° C. by blowing 101/h air through the heated sample for 168 and/or 216 hrs in the presence of 7 wt % B100. Viscosity versus time is measured. The test can be found at www.cectests.org.

Examples 1-11 and Comparative Examples 1-4 were evaluated in the Oxidation Test for Engine Oils Operating in the Presence of Biodiesel Fuel, CEC L-109-14, which is incorporated herein by reference. The test results are shown in Table 4 below. The test results indicate that examples 1-11, those containing a Mannich condensation product, alone or in combination with a EC treated dispersant, polysuccinimide, or borated dispersant show superior viscosity control performance in the presence of biodiesel than EC treated or borated dispersants alone (Comparatives Examples 1-4).

TABLE 4

| Sample | Dispersant (actives) | Relative KV100 |
|---|---|---|
| Example 1 | Mannich condensation product (3.3 wt. %) | 8.89 |
| Example 2 | Mannich condensation product (4.4 wt. %) | 5.72 |
| Example 3 | Mannich condensation product (0.83 wt. %); ethylene carbonate post-treated polyisobutenyl succinimide (2.28 wt. %) | 31.50 |
| Example 4 | Mannich condensation product (0.55 wt. %); ethylene carbonate post-treated polyisobutenyl succinimide (3.42 wt. %) | 23.00 |
| Example 5 | Mannich condensation product (0.83 wt. %); ethylene carbonate post-treated polyisobutenyl succinimide (3.14 wt. %) | 18.60 |
| Example 6 | Mannich condensation product (1.65 wt. %); ethylene carbonate post-treated polyisobutenyl succinimide (2.28 wt. %) | 11.9 |
| Example 7 | Mannich condensation product (2.2 wt. %); ethylene carbonate post-treated polyisobutenyl succinimide (1.71 wt. %) | 6.40 |
| Example 8 | Mannich condensation product (1.65 wt. %); polysuccinimide (2.36 wt. %) | 1.40 |
| Example 9 | Mannich condensation product (0.83 wt. %); borated bissuccinimide (2.52 wt. %) | 84.00 |
| Comparative Example 1 | ethylene carbonate post-treated polyisobutenyl succinimide (2.28 wt. %) | 777.4 |
| Comparative Example 2 | ethylene carbonate post-treated polyisobutenyl bissuccinimide (4.56 wt. %) | 28.43 |
| Comparative Example 3 | borated bissuccinimide (2.52 wt. %) | 707.5 |
| Comparative Example 4 | borated bissuccinimide (5.04 wt. %) | 509.6 |

While the invention has been described with respect to a limited number of embodiments, the specific features of one embodiment should not be attributed to other embodiments of the invention. No single embodiment is representative of all aspects of the invention. In some embodiments, the methods may include numerous steps not mentioned herein. In other embodiments, the methods do not include, or are substantially free of, steps not enumerated herein. Variations and modifications from the described embodiments exist. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A lubricating oil composition contaminated with at least about 0.3 wt % of a biodiesel fuel or a decomposition product thereof, based on the total weight of the lubricating oil composition, wherein the lubricating oil composition comprises:

a. a major amount of base oil of lubricating viscosity; and b. from 0.55 to 4.95 wt. % on an actives basis of a Mannich condensation product, wherein the Mannich condensation product is of the formula 7

Formula 7

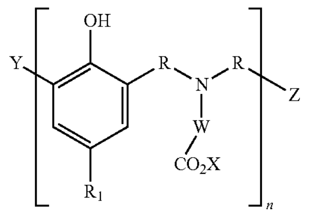

I wherein each R is independently —CHR'—, wherein R' is branched or linear alkyl having one to about 10 carbon atoms, cycloalkyl having from about 3 carbon atoms to about 10 carbon atoms, aryl having from about 6 carbon atoms to about 10 carbon atoms, alkaryl having from about 7 carbon atoms to about 20 carbon atoms, or aralkyl having from about 7 carbon atoms to about 20 carbon atoms, $R_1$ is a polyisobutyl group derived from polyisobutene containing at least about 70 wt. % methylvinylidene isomer and having a number average molecular weight in the range of about 400 to about 2,500;

X is hydrogen, an alkali metal ion, or alkyl having one carbon atom to about 6 carbon atoms;

W is $[CHR'']—_m$, wherein each R'' is independently H, alkyl having one carbon atom to about 15 carbon atoms, or a substituted-alkyl having one carbon atom to about 10 carbon atoms and one or more substituents selected from the group consisting of amino, amido, benzyl, carboxyl, hydroxyl, hydroxyphenyl, imidazolyl, imino, phenyl, sulfide, or thiol; and m is an integer from one to 4;

Y is hydrogen, alkyl having one carbon atom to about 10 carbon atoms, —CHR'OH, wherein R' is as defined above, or of formula 8:

Formula 8

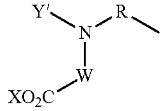

wherein Y' is —CHR'OH, wherein R' is as defined above; and R, X, and W are as defined above;

Z is hydroxyl, a hydroxyphenyl group of the formula 9:

Formula 9

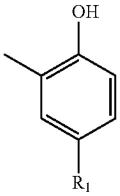

or of formula 10:

Formula 10

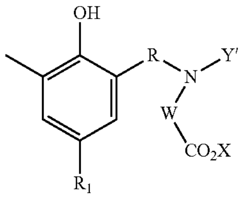

wherein R, $R_1$, Y', X, and W are as defined above, and n is an integer from 0 to 20, with the proviso that when n=0, Z must be of formula 10 as defined above, and c. optionally at least one dispersant present at from 0.85 to 5.13 wt. % on an actives basis.

2. The lubricating oil composition of claim 1, wherein the Mannich condensation product is prepared by the condensation of:

a. a polyisobutyl-substituted hydroxyaromatic compound, wherein the polyisobutyl group is derived from polyisobutene containing at least about 70 wt. % methylvinylidene isomer and has a number average molecular weight of from about 400 to about 2,500, b. an aldehyde, c. an amino acid or ester derivative thereof, and d. an alkali metal base.

3. The lubricating oil composition of claim 2, wherein the polyisobutyl group of the polyisobutyl-substituted hydroxyaromatic compound is derived from polyisobutene containing at least about 90 wt. % methylvinylidene isomer.

4. The lubricating oil composition of claim 2, wherein the polyisobutyl group of the polyisobutyl-substituted hydroxyaromatic compound has a number average molecular weight in the range of from about 500 to about 2,500.

5. The lubricating oil composition of claim 2, wherein the aldehyde is formaldehyde or paraformaldehyde, the alkali metal base is an alkali metal hydroxide and the amino acid is glycine.

6. The lubricating oil composition of claim 1, wherein the dispersant is post-treated.

7. The lubricating oil composition of claim 6, wherein the post-treated dispersant is a boron post-treated dispersant.

8. The lubricating oil composition of claim 7, wherein the boron post-treated dispersant is a borated succinimide.

9. The lubricating oil composition of claim 6, wherein the post-treated dispersant is an ethylene carbonate post-treated succinimide dispersant.

10. The lubricating oil of claim 1, wherein the dispersant is a polysuccinimide.

11. The lubricating oil composition of claim 1 further comprising at least one additive selected from the group consisting of antioxidants, antiwear agents, detergents, rust inhibitors, demulsifiers, friction modifiers, multi-functional additives, viscosity index improvers, pour point depressants, foam inhibitors, metal deactivators, dispersants, corrosion inhibitors, lubricity improvers, thermal stability improvers, anti-haze additives, icing inhibitors, dyes, markers, static dissipaters, biocides and combinations thereof.

12. The lubricating oil composition of claim 1, wherein the sulfated ash content of the lubricating oil composition is at most about 2.0 wt. %, based on the total weight of the lubricating oil composition.

13. The lubricating oil composition of claim 1, wherein the biodiesel fuel comprises an alkyl ester of a long chain fatty acid.

14. The lubricating oil composition of claim 13, wherein the long chain fatty acid comprises from about 12 carbon atoms to about 30 carbon atoms.

15. The lubricating oil composition of claim 1, wherein the amount of the biodiesel fuel or decomposition products thereof is present in the lubricating oil composition at from about 0.3 wt. % to about 20 wt. %, based on the total weight of the lubricating oil composition.

16. The lubricating oil composition of claim 1, wherein the base oil has a kinematic viscosity from about 4 cSt to about 20 cSt at 100° C.

* * * * *